(12) United States Patent
De Meyer et al.

(10) Patent No.: US 8,187,992 B2
(45) Date of Patent: May 29, 2012

(54) CATALYST AND METHOD FOR PREPARING AROMATIC CARBOXYLIC ACIDS

(75) Inventors: Herman Jozef Claudius De Meyer, Brasschaat (BE); Johannes Maria Franciscus Sijben, Etten-leur (NL)

(73) Assignee: Process Design Center B.V., Breda (NL)

( * ) Notice: Subject to any disclaimer, the term of this patent is extended or adjusted under 35 U.S.C. 154(b) by 1096 days.

(21) Appl. No.: 11/793,468

(22) PCT Filed: Dec. 20, 2005

(86) PCT No.: PCT/NL2005/000876
§ 371 (c)(1),
(2), (4) Date: Dec. 28, 2007

(87) PCT Pub. No.: WO2006/068471
PCT Pub. Date: Jun. 29, 2006

(65) Prior Publication Data
US 2009/0088586 A1    Apr. 2, 2009

Related U.S. Application Data

(60) Provisional application No. 60/638,021, filed on Dec. 20, 2004, provisional application No. 60/654,986, filed on Feb. 22, 2005.

(51) Int. Cl.
*B01J 29/06*    (2006.01)

(52) U.S. Cl. .............. 502/62; 502/63; 502/64; 502/66; 502/74

(58) Field of Classification Search ............. 502/62, 502/63, 64, 66, 74
See application file for complete search history.

(56) References Cited

U.S. PATENT DOCUMENTS

| 6,034,269 A | 3/2000 | Turner et al. |
| 6,649,791 B2 | 11/2003 | Srinivas et al. |
| 2002/0028968 A1 | 3/2002 | Graham et al. |
| 2003/0008770 A1 | 1/2003 | Srinivas et al. |

FOREIGN PATENT DOCUMENTS

| EP | 0 041 784 | 12/1981 |
| WO | WO 98/38150 | 9/1998 |

OTHER PUBLICATIONS

Chavan, S. et al. "A novel zeolite-encapsulated $\mu_3$-oxo Co/Mn cluster catalyst for oxidation of *para*-xylene to terephthalic acid." *Chemical Communications*, vol. 12, 2001, pp. 1124-1125.

Chavan S. et al. "Selective oxidation of *para*-Xylene to Terephthalic Acid by $\mu_3$-Oxo-Bridged Co/Mn Cluster Complexes Encapsulated by Zeolite-Y." *Journal of Catalysts*, vol. 204, 2001, pp. 409-419.

Chisem, I. et al. "Catalytic oxidation of alkyl aromatics using a novel silica supported Schiff base complex." *Chemical Communications*, vol. 18, 1998, pp. 1949-1950.

*Primary Examiner* — Elizabeth Wood
(74) *Attorney, Agent, or Firm* — Weingarten, Schurgin, Gagnebin & Lebovici LLP

(57) ABSTRACT

The invention is directed to a catalytic principle based on zeolite crystallites attached to support or incorporated in a matrix and a catalytically active principle incorporated in the zeolite, the said crystallites having a diameter of between 20 and 300 nm and said catalytically active principle having a formula corresponding to: $CoMn_2(O)(R—COO)_6\ L1_{k1}\ L2_{k2}$ wherein: R is an optionally substituted C1-C4 alkyl; L1 is an optionally substituted nitrogen containing carboxylic acid or salts thereof; L2 is selected from the group consisting of H2O, an optionally substituted C1-C4 alkyl containing carboxylic acid, an optionally substituted C5-C6 cycloalkyl or heterocycle, an optionally substituted C5-C6 heteroaryl or aryl; and k1+k2=3; wherein the zeolite has an Si/Al atomic ratio of at least 8, as well as to a method for the oxidation of alkyl aromatics compounds employing the catalytic principle.

12 Claims, 3 Drawing Sheets

CATALYST AND METHOD FOR PREPARING AROMATIC CARBOXYLIC ACIDS

This application is a §371 national phase filing of PCT/NL2005/000876 filed Dec. 20, 2005; and claims priority to U.S. application 60/638,021 filed Dec. 20, 2004, and to U.S. application 60/654,986 filed Feb. 22, 2005.

FIELD OF THE INVENTION

The present invention relates generally to the field of process chemistry. More in particular the invention pertains to novel catalysts useful in the preparation of aromatic carboxylic acids and to a method for preparing aromatic carboxylic acids.

BACKGROUND OF THE INVENTION

Aromatic carboxylic acids, such as benzoic acid, phthalic acid, terephthalic acid, trimethyl benzoic acids, naphthalene dicarboxylic acids and the like, are used widely as intermediates in the chemical industry. Aromatic carboxylic acids are prepared by oxidation of their corresponding alkyl aromatic compounds (see Suresh, A., "Engineering Aspects of Industrial Liquid-Phase Air Oxidation of Hydrocarbons," Ind. Eng. Chem., Vol. 39: p. 3958-3997, (2000)). For instance, terephthalic acid is prepared by oxidation of p-xylene, as shown in the schematic below:

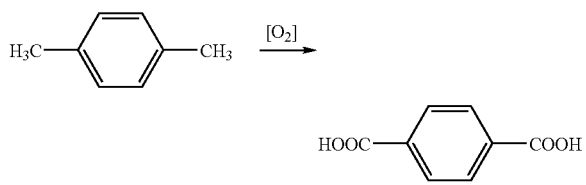

Terephthalic acid, TPA (1,4-benzenedicarboxylic acid), is of commercial interest to the polymer industry because of its use in the manufacture of saturated polyesters, such as polyethylene terephthalate (PET), 1,2-ethanediol, and copolymers thereof. Worldwide production of TPA and its corresponding dimethyl ester, dimethyl terephthalate, ranked about 25th in tonnage of all chemicals produced in 1992, and about 10th of all organic chemicals.

As shown in the scheme below, the oxidation of p-xylene is a radical initiated, step-wise reaction which produces two main intermediates, p-toluic acid and 4-formyl-benzoic acid.

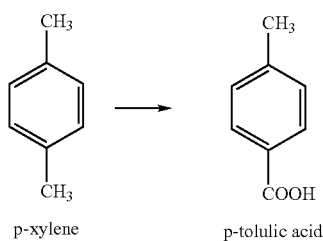

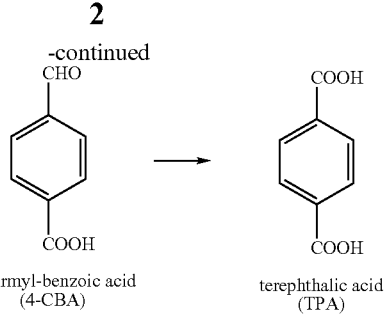

Incomplete oxidation of 4-formyl-benzoic acid (4-CBA) leads to contamination of TPA purity. Removal of 4-CBA is complicated by the fact that it co-crystallizes with TPA due to its structural similarity with TPA. Contamination with 4-CBA can be substantial; for instance, there are production processes that yield a TPA stock which have approximately 5000 ppm of 4-CBA (Perniconea et al., "An investigation on Pd/C industrial catalysts for the purification of terephthalic acid," Catalysis Today, Vol. 44: p. 129-135 (1998)). Thus, subsequent purification steps after TPA production are often necessary in order to attain TPA feedstock of sufficient purity for high-grade polyester synthesis (see Matsuzawa, K. et al., "Technological Development of Purified Terephthalic Acid," Chemical Economy & Engineering Review, Vol. 8 (9): p. 25-30 (1976)).

There are numerous process methods available for manufacturing TPA, each of which have varying production and purity yields for TPA. Most of these processes involve oxidation of p-xylene with an oxygen source e.g. air or $O_2$ gas, in the presence of liquid phase, homogeneous catalysts containing at least cobalt and/or manganese metals. In addition, most of these processes are conducted in the presence of an acidic solvent, such as acetic acid, and as a rule employ corrosive bromine promoters as a radical source e.g. HBr, NaBr, or other metal bromines. Thus, these processes are typically conducted in expensive, titanium-clad reactors that can accommodate such harsh reaction conditions. Representative methods for manufacturing TPA are described in the following patents and publications, the disclosures of all of which are incorporated herein by reference.

U.S. Pat. Nos. 2,833,816 and 3,089,906 report a process for oxidizing a polyalkyl aromatic compound with $O_2$ in acetic acid solvent using a metal bromine catalyst.

U.S. Pat. No. 4,786,753 reports a process for oxidizing di- and trimethyl benzenes in the presence of an aliphatic acid in the presence of a nickel, zirconium, and manganese catalyst system with a bromine source.

U.S. Pat. No. 4,877,900 report a two-stage oxidation process for p-xylene with molecular oxygen in the presence of a heavy metal catalyst and bromine, wherein the second stage involves post-oxidation with molecular oxygen and is conducted at a higher temperature then the first stage.

U.S. Pat. No. 4,892,970 reports a two-stage process for the oxidation of alkyl benzenes in the presence of a cobalt, nickel, or zirconium metal catalyst and bromine, wherein additional bromine is added to a second stage of the process.

U.S. Pat. No. 5,453,538 reports a process for oxidizing dimethyl benzene with molecular oxygen in a $C_1$-$C_6$ aliphatic carboxylic acid solvent with a cobalt, manganese, and cerium catalyst and a bromine source.

U.S. Pat. Nos. 5,596,129 and 5,696,285 reports a process for oxidizing alkyl benzenes by supplying a nearly pure $O_2$ gas source to the reactor. These processes are conducted in an acetic acid/water medium and utilizes a cobalt, manganese, and bromine catalyst.

Cincotti, A. et al. ("Kinetics and related engineering aspects of catalytic liquid-phase oxidation of p-xylene to terephthalic acid," Catalysis Today, Vol. 52: p. 331-347, (1999)) reports a kinetic model for TPA production. This study evaluated the oxidation of p-xylene in a methyl benzoate solvent using cobalt naphthenate as a catalyst. P-tolualdehyde was used as a promoter source and either pure oxygen or air was the oxidation source.

Dunn, J. et al. ("Terephthalic Acid Synthesis in High-Temperature Liquid Water, Ind. Eng. Chem. Res., Vol. 41: p. 4460-4465, (2002)) reports a TPA synthesis process in liquid water at temperatures ranging from 250 to 300° C. This process utilizes hydrogen peroxide, instead of air or $O_2$, as an oxidant.

The following catalysts were evaluated in the study: manganese bromide, cobalt bromide, manganese acetate, nickel bromide, hafnium bromide, and zirconium bromide.

Partenheimer, W. et al., ("The effect of zirconium in metal/bromide catalysts during the autoxidation of p-xylene," Journal of Molecular Catalysis A: Chemical, Vol. 206: p. 105-119, (2003)) reports the oxidation of p-xylene in acetic acid medium with a zirconium catalyst and either a cobalt, manganese/bromide, nickel/manganese/bromide, or cobalt/manganese/bromide catalyst.

The less corrosive bromoanthracenes, in comparison to NaBr or HBr, have been employed as a bromide source in the oxidation of p-xylene. Saha et al. ("Bromoanthracenes and metal co-catalysts for the autoxidation of para-xylene," Journal of Molecular Catalysis A: Chemical, Vol. 207: p. 121-127, (2004)) reports the oxidation of p-xylene in acetic acid using 9,10-dibromoanthracene or 9-bromoanthracene in the presence of $Co(OAc)_2$ and either a $Mn(OAc)_2$, $Ce(OAc)_3$, or $ZrOCl_2$ co-catalyst.

Methods for TPA manufacturing that use solid catalysts include Chavan et al. ("Selective Oxidation of para-Xylene to Terephthalic Acid by $\mu_3$-oxo-bridged Co/Mn Cluster Complexes Encapsulated in Zeolite-Y," Journal of Catalysis, Vol. 24: p. 409-419, (2001)) and Srinivas et al. (U.S. Pat. No. 6,649,791 and U.S. Patent Application Publication No. 2003/0008770). In these methods, solid catalysts of $\mu_3$-oxo-bridged Co/Mn cluster complexes, $[Co_3(O)(CH_3COO)_6(pyridine)_3]^+$, $[Mn_3(O)(CH_3COO)_6(pyridine)_3]^+$, and $CoMn_2(O)(CH_3COO)_6(pyridine)_3$, are encapsulated in Zeolite-Y and the oxidation process was carried out in an acetic acid/water solvent using NaBr as a radical initiator.

TPA has also been prepared employing a solid catalyst without the use of bromide ions. Jacob et al. (Journal Applied Catalysis A: General, Vol. 182: p. 91-96, (1999)) described the aerial oxidation of p-xylene over Zeolite-encapsulated salen, saltin, and salcyhexen complexes of cobalt or manganese using t-butyl hydroperoxide as the initiator. This process converts up to 50-60% of p-xylene; however, the yields of TPA are low and the main product attained is p-toluic acid.

Currently, there exists a need for methods of synthesizing aromatic carboxylic acids with sufficiently high yields and suitable purity for subsequent high-grade manufacturing processes, so as to obviate the need for additional purification steps. In addition, there exists a need for methods that avoid the use of corrosive feed materials or other process materials which may be harmful to the environment, such as acetic acid, NaBr, or HBr.

SUMMARY OF THE INVENTION

The present invention concerns novel solid catalysts, and their use in the preparation of an aromatic carboxylic acid by oxidation of an alkyl aromatic compound. The invention also provides a one-step method using such a catalyst, which circumvents the need for subsequent purification procedures e.g. hydrogenation, for the preparation of high-grade alkyl aromatic compounds. Embodiments of the present method avoid the use of corrosive inorganic bromine reagents by employing more environmentally sensible organic bromated reagents. The novel catalyst itself consists of small crystallites of the catalytic principle, with a specified narrow size distribution, which are attached to or encapsulated in a support, more in particular encapsulated within a meso-porous, possibly functionally enhanced matrix material.

The present invention is drawn to a catalytic principle based on zeolite crystallites attached to support or incorporated in a matrix and a catalytically active principle incorporated in the zeolite, the said crystallites having a diameter of between 20 and 300 nm and said catalytically active principle having a formula corresponding to:

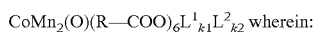 wherein:

R is an optionally substituted $C_1$-$C_4$ alkyl;
$L^1$ is an optionally substituted nitrogen containing carboxylic acid or salts thereof;
$L^2$ is selected from the group consisting of $H_2O$, an optionally substituted $C_1$-$C_4$ alkyl containing carboxylic acid, an optionally substituted $C_5$-$C_6$ cycloalkyl or heterocycle, an optionally substituted $C_5$-$C_6$ heteroaryl or aryl; and
k1+k2=3;
wherein the zeolite has an Si/Al atomic ratio of at least 8. Embodiments include catalysts of the above formula where R is —$CH_3$ or —$C_2H_5$; where $L^1$ is picolinic acid, nicotinic acid, or iso-nicotinic acid; and where $L^2$ is $CH_3COOH$ or $H_2O$.

The present invention is also drawn to a catalytic principle having a formula corresponding to $CoMn_2(O)(R—COO)_{6-k3}L^3_{k3}L^4_{k4}$, wherein:

R is an optionally substituted $C_1$-$C_4$ alkyl;
$L^3$ is an optionally substituted nitrogen containing carboxylate;
$L^4$ is selected from the group consisting of $H_2O$, an optionally substituted nitrogen containing carboxylic acid, an optionally substituted $C_1$-$C_4$ alkyl containing carboxylic acid, an optionally substituted $C_5$-$C_6$ cycloalkyl or heterocycle, and an optionally substituted $C_5$-$C_6$ heteroaryl or aryl;
k3 is 1, 2, or 3; and
k3+k4=3.

Preferred embodiments include catalytic principles of the above formula where R is —$CH_3$ or —$C_2H_5$; where $L^3$ is 1-pyridine-COO—, 2-pyridine-COO—, or 3-pyridine-COO—; and where $L^4$ is picolinic acid, nicotinic acid, i-nicotinic acid, $CH_3COOH$, or $H_2O$.

The invention resides therein, that the specific catalytically active principle is incorporated within the specifically selected zeolite, which zeolite is preferably characterized in that it has an Si/Al atomic ratio of at least 8. Preferably the ratio is at most 12. Preferably the size of the channels is such, that the catalytically active principle is too large to migrate through the channels. However, the crossings of the channels are sufficiently large to trap the catalytically active principle. In the invention the said principle is accordingly synthesized in place, i.e. at said crossings, which is the preferred method, although it is also possible that the zeolite is synthesized around the said complete principle.

Suitable channel diameters are within the range of up to 8 Å.

The zeolite crystallites are quite small, namely between 20 and 300 nm. With larger crystallites diffusion limitation may occur, resulting in decrease of activity and selectivity, thereby defeating one of the objects of the invention, namely the possibility to produce aromatic carboxylic acids, such as therephtalic acids without the need to have subsequent purification.

Another aspect of the invention resides in the matrix encapsulation. This matrix supports the crystallites and may have a meso-porous structure. The support or matrix material should preferably have no or limited functionality in the oxidation reaction, and be such that it does not hinder the diffusion of reaction components into or out of the crystallites. Suitable matrix materials include mesoporous silica, carbon, carbon nanotubes and the like.

Catalytic principles presented herein have the metal complex hosted within a possibly functionally enhanced zeolite, which include, but are not limited to MEI, beta (*BEA), and also including members of the associated disorder families, such as fibrous and the like, micro-porous structures based on the above zeolites and mixtures thereof. For a detailed explanation of the structural similarities among zeolites and a list of references with specific structural information about zeolites, see, for example, U.S. Pat. Nos. 4,344,851; 4,503,023; 4,840,779; and Baerlocher et al., "Atlas of Zeolite Framework Types," ELSEVIER Fifth Revised Edition, (2001)). Preferred zeolites used to host the presented metal complexes include beta zeolite.

The phrase "alkyl" refers to hydrocarbyl groups comprising from 1 to 20 carbon atoms. The phrase "alkyl" includes straight chain alkyl groups such as methyl, ethyl, propyl, and the like. The phrase also includes branched chain isomers of straight chain alkyl groups. Additionally, alkyl groups can be optionally substituted according to the definition below. Thus, alkyl groups includes primary alkyl groups, secondary alkyl groups, and tertiary alkyl groups. Presently, preferred alkyl groups include unsubstituted alkyl groups having from 1 to 4 carbon atoms while even more preferred such groups have from 1 to 3 carbon atoms.

The phrase "substituted" refers to an atom or group of atoms that has been replaced with another substituent. The phrase "substituted" includes any level of substitution, i.e. mono-, di-, tri-, tetra-, or penta-substitution, where such substitution is chemically permissible. Substitutions can occur at any chemically accessible position and on any atom, such as substitution(s) on carbons. For example, substituted compound are those where one or more bonds to a hydrogen or carbon atom(s) contained therein are replaced by a bond to non-hydrogen and/or non-carbon atom(s).

The phrase "nitrogen containing carboxylic acid" refers to a compound comprising at least one carboxylic acid moiety (—COOH) and at least one optionally substituted nitrogen atom. Nitrogen containing carboxylic acid compounds embrace acyclic and cyclic structures, wherein the nitrogen can optionally be a ring member. For instance, nitrogen containing carboxylic acid encompass pyridines, picolines, pyrimidines, piperidines, and the like that comprise at least one —COOH. Preferable nitrogen containing carboxylic acids include picolinic acid, nicotinic acid, and i-nicotinic (the structures of which are shown below).

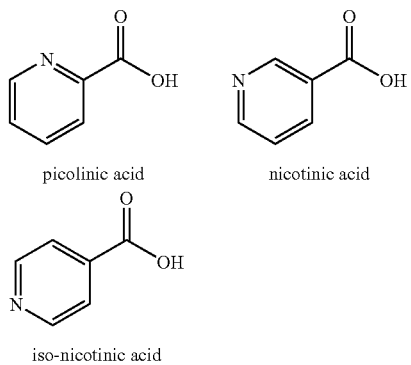

picolinic acid    nicotinic acid iso-nicotinic acid

The phrase "$C_1$-$C_4$ alkyl containing carboxylic acid" refers to a compound comprising at least one carboxylic acid moiety (—COOH) and at least one optionally substituted $C_1$-$C_4$ alkyl group. The phrase embraces straight chain, branched, and cyclic $C_1$-$C_4$ alkyl groups comprising at least one —COOH. Furthermore, the phrase also embraces $C_1$-$C_4$ alkyl groups containing any level of saturation. For instance, $C_1$-$C_4$ alkyl containing carboxylic acid compounds encompass acetic acid, propionic acid, butyric acid, and halogenated substitutions thereof, such as $CH_2FCOOH$, $CH_2ClCOOH$, $CH_2BrCOOH$, and the like. Preferable $C_1$-$C_4$ alkyl containing carboxylic acid include $CH_3COOH$.

The phrase "nitrogen containing carboxylate" refers to a compound comprising at least one carboxylate moiety (—COO$^-$) and at least one optionally substituted nitrogen atom. Nitrogen containing carboxylate compounds embrace acyclic and cyclic structures, wherein the nitrogen can optionally be a ring member. For instance, nitrogen containing carboxylates encompass pyridines, picolines, pyrimidines, piperidines, morpholine and the like that comprise at least one —COO$^-$. Preferable nitrogen containing carboxylates include 1-pyridine-COO$^-$, 2-pyridine-COO$^-$, and 3-pyridine-COO$^-$ (the structures of which are shown below).

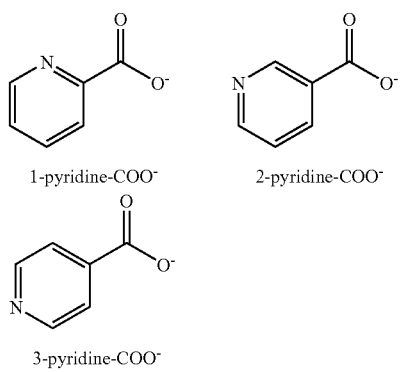

1-pyridine-COO$^-$    2-pyridine-COO$^-$ 3-pyridine-COO$^-$

The phrase "cycloalkyl" refers to a saturated or unsaturated alicyclic moiety having 1 to 20 carbon atoms. Cycloalkyl groups include cyclohexyl and cycloheptyl. The phrase "substituted cycloalkyl" refers to a cycloalkyl group that is substituted according to the definition provided above. Substituted cycloalkyl groups can have one or more atom substituted with straight or branched chain alkyl groups and can further comprise cycloalkyl groups that are substituted with other rings including fused rings. Representative substituted cycloalkyl groups may be mono-substituted such as, but not limited to 2-, 3-, 4-, 5-substituted cyclohexyl groups or mono-substituted groups, such as alkyl or halo groups The phrase "heterocycle" or "heterocyclic" refers to both aromatic and nonaromatic ring hydrocarbyl compounds. Heterocyclic groups include monocyclic, and bicyclic compounds containing 3 or more ring members of which one or more is a heteroatom such as, but not limited to, N and O. Examples of heterocyclyl groups include, but are not limited to, unsaturated 3 to 6 membered rings containing 1 to 3 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e.g. 4H-1,2,4-triazolyl, 1H-1,2,3-triazolyl, and 2H-1,2,3-triazolyl); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 3 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, and 1,2,5-oxadiazolyl); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, and benzoxazinyl (e.g. 2H-1,4-benzoxazinyl). Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, and isoxazole. The phrase "substituted heterocycle" or "substituted heterocyclic" refers to a heterocyclic group that is substituted according to the definition provided above. Examples of substituted heterocyclic groups include, but are not limited to, 2-methylbenzimidazolyl, 5-methylbenzimidazolyl, 1-methyl piperazinyl, 2-chloropyridyl, and the like.

The phrase "aryl" refers to aromatic radicals comprising from 3 to 20 carbon atoms. Aryl groups include, but are not limited to, phenyl, biphenyl, anthracenyl, and naphthenyl. The phrase "substituted aryl group" refers to an aryl group that is substituted according to the definition provided above. For example, substituted aryl groups may be bonded to one or more carbon atom(s), oxygen atom(s), or nitrogen atom(s), and also includes aryl groups in which one or more aromatic carbons of the aryl group is bonded to a substituted and/or unsubstituted alkyl, alkenyl, or alkynyl group. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, and hydroxyphenyl among others. Preferably, aromatic groups are substituted with alkyl, carboxylic acid (—COOH), and/or carboxylate groups (—COO$^-$).

The phrase "heteroaryl" refers to a 3 to 20-membered aromatic ring consisting of carbon atoms and heteroatoms, such as N and O or (ii) an 8- to 10-membered bicyclic or polycyclic ring system consisting of carbon atoms and heteroatoms, such as N and O, wherein at least one of the rings in the bicyclic system is an aromatic ring. The heteroaryl ring may be attached at any heteroatom or carbon atom. Representative heteroaryl compounds include, for example, pyridyl, pyrazinyl, pyrimidinyl, pyridooxazolyl, pyridazooxazolyl, and pyrimidooxazolyl. The phrase "substituted heteroaryl" refers to a heteroaryl group that is substituted according to the definition provided above.

An aspect of the invention is drawn to methods or manufacturing processes for the preparation of an aromatic carboxylic acid by contacting an alkyl aromatic compound with an oxygen source in the presence of a catalyst as provided herein. Preferably, such methods are performed in the presence of a solvent in which said aromatic carboxylic acid is soluble.

The present invention is also drawn to a one-step process for preparing an aromatic carboxylic acid comprising contacting an alkyl aromatic compound with an oxygen source in the presence of a catalyst as provided herein. Such one-step processes are highly efficient, thus circumventing the need for subsequent purification procedures e.g. hydrogenation or crystallization, in the preparation of high-grade alkyl aromatic compounds.

Preferably, the present methods are directed to the preparation of terephthalic acid by oxidizing p-xylene in the presence of a catalyst provided herein. Other aromatic carboxylic acids which may be prepared include iso-terephthalic acid and naphthalene carboxylic acid.

The phrase "aromatic carboxylic acid" refers to any optionally substituted aromatic group that comprises at least one carboxylic acid (—COOH) substituent. Representative aromatic carboxylic acids include, but are not limited to, benzoic acid, isophthalic acid, phthalic acid, terephthalic acid, trimethyl benzoic acids, naphthalene dicarboxylic acids, and the like. Preferred aromatic carboxylic acids include terephthalic acid (TPA).

The phrase "alkyl aromatic" refers to any optionally substituted aromatic group, as defined above, comprising at least one optionally substituted alkyl group, as defined above. Representative alkyl aromatic compounds include, but are not limited to, toluene, xylene (p-xylene), trimethyl benzene, methylnaphthalene, dimethylnaphthalene, and the like. Preferred alkyl aromatic compounds include p-xylene.

The phrase "oxygen source" refers to any source which supplies oxygen directly or indirectly in the presently claimed method. An oxygen source may be fed from an external source or generated in situ. Preferably, an oxygen source is provided in the same phase as the solvent. For instance, $O_2$ may be provided to p-xylene liquid solvent by absorption from a supercritical solvent saturated in oxygen, from gaseous oxygen at elevated pressure through a selective membrane. Alternatively, $O_2$ may absorbed into a solvent by absorption out of an oxygen containing gas at high pressure, such as air or molecular oxygen, and fed directly into the reactor and/or to a recycled stream from the reactor by diffusion through a selective membrane. Gaseous $O_2$ may also be provided by evaporation or dissolution of liquid oxygen and absorption into a solvent, including supercritical fluids, and fed into the reactor medium from a saturated solution directly or indirectly, depending on the characteristics of the oxygen solvent. Representative oxygen sources include, but are not limited to, air, gaseous and liquid molecular oxygen, hydrogen peroxide, and the like. Preferably, oxygen sources used herein comprise at least 99% oxygen, at least 95%, at least 90%, at least 85%, or at least 80% oxygen.

Embodiments of the invention relate to methods of preparing aromatic carboxylic acids in the presence of a solvent in which said aromatic carboxylic acid is soluble. Preferably, the solvent used in the present methods is the same as the alkyl aromatic compound. For example, in embodiments drawn to methods for preparing TPA, it is preferred that both the solvent and the alkyl aromatic compound is p-xylene.

Preferable embodiments include performing the present methods in the absence of an acidic solvent. Acidic solvents, such as acetic acid, are highly corrosive and thus, steel-clad reactors are currently being used to accommodate reactions employing said solvents. Methods presented herein provide an improvement over the art, in part, avoid the use of steel-clad reactors by performing the reactions in a non-acidic solvent.

The phrase "solvent" refers to a substance, usually a liquid, which is capable of dissolving another substance, such as an alkyl aromatic compound. Solvents used herein have a purity of at least 99%, of at least 97%, or of at least 95%. Preferred solvents for the present methods include p-xylene.

The phrase "soluble" refers to solubility of a given compound, such as the produced aromatic carboxylic acid, in a solvent. Solubility can be measured in units of g/L or moles/L, wherein such measurements are taken at temperatures ranging from 150° C. to 250° C. and at pressures ranging from 20 atm to 50 atm. In a preferred embodiment, the solubility of terephthalic acid in p-xylene at 25° C. and 1 atm is 0.0028 g/L.

The phrase "acidic" refers to solvents or solutions having a pH lower than 7, such as 5 or lower, and further such as 3 or lower.

The reaction rate of methods of producing aromatic carboxylic acids using an invention catalyst can be accelerated by the addition of a halogen containing agent. The phrase "halogen containing agent" refers to an organic or inorganic agent which comprises a halogen ion, such as F, Cl, Br, and I. Preferable halogen containing agents are capable of mediating radical formation and hydrogen abstraction without explicit involvement of free halogen radicals or ions such as F., F⁻, Cl., Cl⁻, Br., or Br⁻. Exemplary halogen containing agents include hydrocarbyl bromated agents, such as bromobenzene, 9-bromoanthracene, and 9,10-dibromoanthracene.

The phrase "hydrocarbyl" refers to any organic radical having a directly attachable carbon atom. Hydrocarbyl groups include saturated and unsaturated hydrocarbons, straight and branched chain aliphatic hydrocarbons, cyclic hydrocarbons, and aromatic hydrocarbons. Representative hydrocarbyl groups include alkyls, alkenyls, alkynyls, cycloalkyls, aryls (such as anthracene), and arylalkyls.

DETAILED DESCRIPTION OF THE INVENTION

I. Invention Catalysts

A. Preparation of Invention Catalytic Principle

Figure 1:
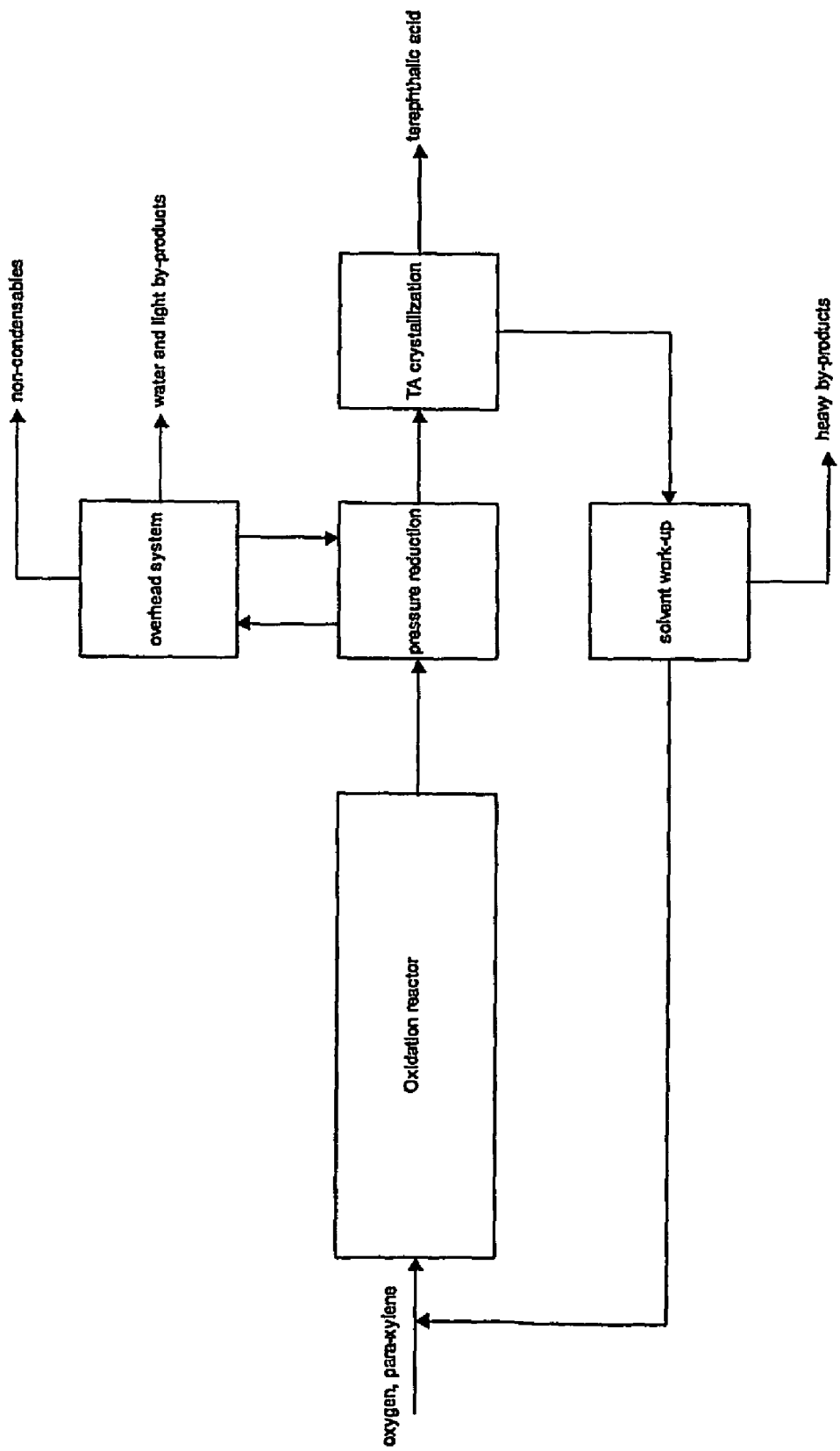
FIG. 1 and FIG. 2 are a schematic depicting an exemplary method for oxidation of alkyl aromatic compounds. Further details regarding the oxidation of p-xylene to produce terephthalic acid is provided in the Examples below.
Figure 2:
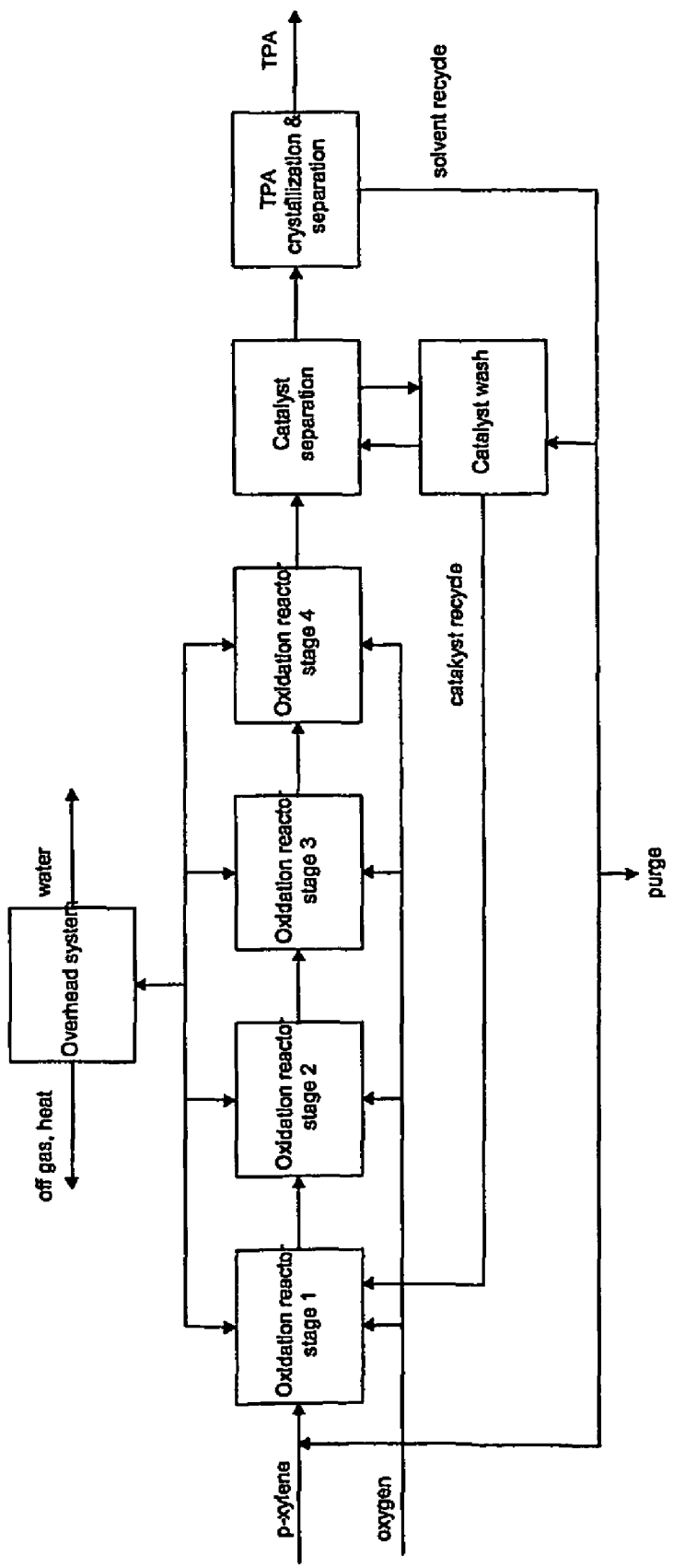
Figure 3:
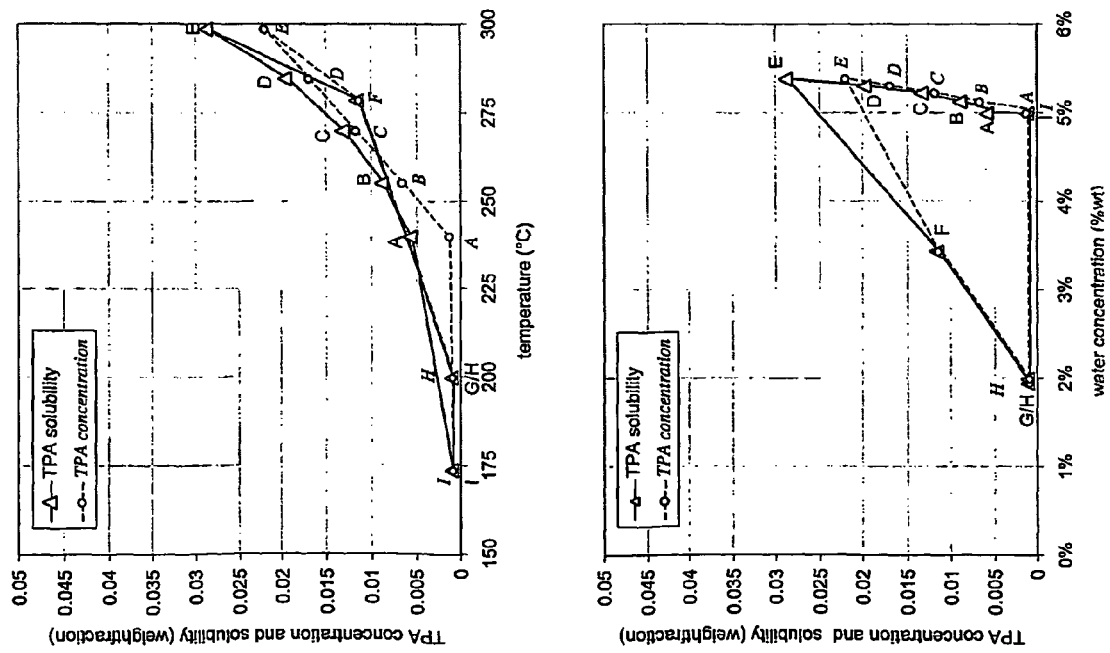
FIG. 3 details the solubility range of the terephthalic acid and the operational concentration range of the catalyst.

The present invention provides novel compositions that have unique catalytic function by stabilizing a catalytic principle corresponding to $CoMn_2(O)(R—COO)_6L^1_{k1}L^2_{k2}$ and $CoMn_2(O)(R—COO)_{6-k3}L^3_{k3}L^4_{k4}$, as described above, in micro-porous zeolite or as clustered aggregates encapsulated by specific synthesis within a zeolite composite structure. The catalyst consists of crystallites of zeolite of appropriate small size embedded in a meso-porous matrix of inert material or attached to a suitable support.

Preferred embodiments of metal complex of the catalysts provided herein include $CoMn_2(O)(CH_3—COO)_6$ $(2-NC_6H_4COOH)_3$ and $CoMn_2(O)(CH_3—COO)_5(1-NC_6H_4COO)(1-NC_6H_4COOH)_2$/beta Zeolite with small crystallites (~100 nm) of in a meso-porous SiC matrix.

Various methods for preparing the components for the presented catalysts are well known to one of skill in the art. For instance, preparative procedures for synthesizing the catalytic principle of the invention catalyst, include those described, for example, in Kennet J. et al. ("Applicable Zeolite Encapsulation Methods Flexible Ligand Method", J. Inclus. Phenom., Vol. 21:159-184 (1995)); Vandermade, A. W. et al. (J. Chem. Soc. Chem. Commun., Vol. 1204 (1983)); and Viswanathan et al. (J. Energy Heat and Mass Transfer, Vol. 8: 281 (1996)). The production of meso-porous zeolite has been reviewed, for example, in Walter G. Klemperer et al. ("Tailored Porous Materials" Chem. Mater. 1999, 11, 2633-2656).

Alternative preparative procedures may be employed for preparing zeolites for use with larger ligands. In instances where the coordinating molecule is large or too inflexible to penetrate the zeolite, the zeolite can be synthesized around the already pre-formed $\mu_3$-oxo bridged metal coordinated complex by the use of structure directing molecules. Such procedures are described, for example, in Mitchell, M. et al. (Z. Phys. B, Vol. 97: 353 (1995)); Lobo, R. et al. (J. Inclusion Phenom. Mol. Recognit. Chem., Vol. 21: 47 (1995)); and Barton, T. J. et al. ("Tailored Porous Materials", Chem. Mater., Vol. 11: 2633-2656 (1999)). A recent review may be found, for example, in Martin P. Attfield ("Microporous materials" Science Progress (2002), 85 (4), 319-345).

In addition, the composition of the invention further includes a zeolite. In preferred embodiments, invention catalysts consist of encapsulated crystallites of a zeolite catalytic principle. Certain zeolites provide catalytic principles that may be more optimal for use in the presently claimed methods. Suitable zeolites for use in the invention have an Si/Al atomic ratio of at least 8. These zeolites are micro-porous materials which comprise pore sizes of up to 8 Å, and preferably having no zeolite cages.

Preferred zeolites are meso-porous beta zeolite (*BEA) with small crystallite size of about 20-200 nm but also including members of the associated disorder families, such as fibrous. Specific embodiments of clustered sites catalysts provided herein include $CoMn_2(O)(CH_3—COO)_6$ $(2-NC_6H_4COOH)_3$ encapsulated in a beta zeolite which is embedded within a meso-porous $SiO_2$ matrix and $CoMn_2(O)(CH_3—COO)_5$ $(1-NC_6H_4COO)(1-NC_6H_4COOH)_2$ hosted in a beta zeolite supported on meso-porous carbon.

A representative method for encapsulating the invention catalytic principle involves creating the "ship-in-bottle" catalytic structure by the "flexible ligand method". This well known method involves ligand diffusion through the pores of an already metal exchanged zeolite. For more detailed discussion of exemplary preparation methods, see, for example Raja et al., J. Catal. Vol. 170, p. 244 (1997); Subbarao et al., Chem. Comm., Vol. 355, (1997); and Balkus et al., J. Inclus. Phenom., Vol. 21: p. 159 (1995).

B. Matrix Encapsulation of Invention Catalysts

The embedding of small crystallites of zeolites into a meso-porous inert matrix in situ during its synthesis is discussed, for example, in J. C. Jansen et al. (Chem. Commun., p. 713 (2001)), in Z. Shan et al. (Chem. Eur. J., 7, p. 1437 (2001)), in J. C. Jansen et al. (Micro. Meso. Mater., 21, p. 213 (1998)) in S. Basso, J. P. Tessonnier, C. Pham-Huu, M. J. Ledoux, French Patent Appl. No. 02-00541 (2002).

The encapsulation provides mechanical strength to the catalytic principle and allows the preparation of the invention catalyst in several different forms for use in fixed bed, slurry particles, membranes and other configurations.

The preferred method will depend both on the zeolite component of the catalytic principle and the encapsulation matrix material. Preparation methods may consist of grafting separately prepared zeolites on the inert matrix material or, alternatively, the composite may be synthesized in situ by adding the appropriate matrix material to a specific zeolite synthesis gel. These methods, such as adapted hydrothermal syntheses are generally known to one skilled in the art. The methodology for synthesis of composites, such as through the hydrothermal process are discussed, for example, in Camblor M. A. et al. ("Characterization of nanocrystalline zeolite Beta", Microporous and Mesoporous Materials 25, p. 59-74 (1998)). Synthesis of zeolite Y encapsulated on SiC is discussed, for example, in G. Clet, J. C. Jansen and H. van Bekkum, (poster at 12th IZC, Baltimore, (1998)), whereas grafting of beta zeolite on SiC is discussed, for example, by S. Feng and T. Bein, (Nature, 368, p. $83^4$ (1994)). M.V. Depositing zeolite crystallites on SiO2 is discussed, for example, in Landau, N. Zaharur, M. Herskowitz, (Appl. Catal. 115, L7-L14 (1994)). A procedure to deposit zeolites on carbon is discussed, for example, in C. Madsen, C. J. H. Jacobsen, (Chem. Commun. 8, p. 673-674 (1999)). Syntheses of highly ordered mesoporous structures by means of the self-assembly of preformed clusters of zeolite nuclei in which surfactant micelles templates are used have been described, for example, in Z. T. Zhang, Y. Han, L. Zhu, R. W. Wang, Y. Yu, S. L. Qiu, D. Y. Zhao, F. S. Xiao, (Angew. Chem., 113, 1298-1301 (2001)) and W. P. Guo, L. M. Huang, P. Deng, Z. Y. Xue, Q. Z. Li, (Microporous Mesoporous Mater., 44, 427-434 (2001)).

Preferred encapsulating matrix materials include mesoporous silica and carbon, such as carbon nanotubes, and SiC.

The in-situ synthesis of the metal complex itself may be realized after the encapsulation of the zeolite in the matrix material. The preferred method for the preparation of the invention catalysts is to create the catalytic principle itself in the matrix as a second production step after encapsulation.

II. Use of Invention Catalysts

Catalysts provided herein can be employed in a variety of synthetic processes. For instance, invention catalysts can be used in the synthesis of a variety of organic compounds, such as, but not limited to, alkyl, alkenyl, alkynyl, cycloalkyl, heterocyclyl, aryl, or heteroaryl containing compounds. Furthermore, invention catalysts may be used in the stereoselective synthesis of organic compounds. Moreover, invention catalysts may be utilized in the preparation of macrocyclic compounds, such as fungicides, antibiotics, natural product mimetics, and the like.

Preferably, invention catalysts are used in the oxidation of alkyl aromatic compounds to produce aromatic carboxylic acids. Various methods for oxidizing alkyl aromatic compounds in the presence of a catalyst are well known to one of skill in the art. Described in the Examples below is a generalized representative procedure, which can vary within the scope of routine experimentation and depending on well-known factors, such as scale of synthesis.

The preparation of aromatic carboxylic acids can be performed in one reactor or a series of reactor. The phrase "reactor" refers to any vessel appropriate for accommodating the oxidation reaction described herein. For example, oxidation of alkyl aromatic compounds can be performed in a single large stirred tank reactor. Alternatively, oxidation of alkyl aromatic compounds can be performed in a continuous series of reactors. For instance, an oxygen source can be provided to each reactor in the series, so as to facilitate highly efficient oxidation of alkyl aromatic compounds. Additionally, reactor series can be lock adjusted, so as to prevent backflow of materials.

Representative reactors which can be used in accordance with methods provided herein include titanium-clad and steel reactors.

The present methods for the preparation of aromatic carboxylic acids can be conducted at temperatures ranging from 200 to 250° C., and at pressures ranging from 280 to 750 psig.

In accordance with methods provided herein, an alkyl aromatic compound is provided to at least one reactor. Alkyl aromatic compounds include aromatic hydrocarbons having at least one oxidizable substituent group capable of being oxidized to a corresponding carboxylic acid or the derivative product. Preferred alkyl aromatic compounds include disubstituted benzene materials having any of a variety of substituents, such as alkyl, hydroxyalkyl, aldehyde, carboalkyl groups, and mixtures thereof. More preferred alkyl aromatic compounds include para-disubstituted benzene derivatives having alkyl groups as substituents. An especially preferred alkyl aromatic compound is p-xylene and/or p-toluic acid.

Typically, an alkyl aromatic compound is provided to at least one reactor in an amount ranging from about 310 kg/s to about 1010 kg/s.

In a preferred embodiment, the present methods are performed in the presence of a solvent wherein the produced aromatic carboxylic acid is soluble. For example, such solvents include, but are not limited to, p-xylene; basic solvents such as chloro-benzene, morpholine, esters of carboxylic acids and the like; carboxylic anhydrides; and acidic solvents, such as acetic acid.

Particularly preferred solvents are those which are the same as the alkyl aromatic compound. For instance, in embodiments drawn to methods for preparing TPA, it is preferred that both the solvent and the alkyl aromatic compound is p-xylene containing from 0 to 18 percent by weight water. In other embodiments drawn to methods for preparing TPA, it is preferred to use a solvent in which both terephthalic acid and the intermediate 4-CBA is soluble. Not wishing to be bound by any particular theory, it is believed that keeping 4-CBA in solution, further oxidation of 4-CBA is facilitated. As a consequence, a larger portion of 4-CBA within the reaction medium is converted to terephthalic acid thereby decreasing the formation of color-precursors. Moreover, the present process circumvents the need for removing 4-CBA from within the solid product precipitate in the reaction medium and allows a one-step preparation of TPA.

Typically, solvent is provided to at least one reactor at a rate ranging from about 310 kg/s to 1010 kg/s.

In accordance with methods provided herein, at least one invention catalyst is provided to at least one reactor. For instance, an invention catalyst can be provided to each reactor as an entrained slurry, a fluidized bed, or installed in various forms of fixed beds, membranes, packing arrangements, etc. in each reactor within a series of reactors. The catalytic principle may be provided alone, or as embedded zeolite crystallites within an inert matrix. Typically, an invention catalyst is provided to at least one reactor in an amount ranging from about 700 per 100 weight parts of p-xylene to 1400 per 100 weight parts of p-xylene (in matrix encapsulated form). Oxidation of alkyl aromatic compounds in the presence of an invention catalyst can occur for a time period ranging from about 8 to about 20 min.

The reaction rate of oxidation methods presented herein are enhanced by the addition of a halogen containing or releasing agent. Preferable halogen containing agents include hydrocarbyl bromated agents, such as 9-bromoanthracene and 9,10-dibromoanthracene. A halogen containing or releasing agent may be added to at least one reactor, such as to each reactor within a series of reactors. In addition, the same or a different halogen containing or releasing agent may be added to each reactor within a series of reactors. Typically, halogen containing or releasing agent is provided to at least one reactor in such an amount that the bromine contents ranges from about 2 to 4.5 weight parts of bromine per 100 weight parts of p-xylene.

In accordance with methods provided herein, an oxygen source is provided to at least one reactor. For instance, an oxygen source can be provided to each reactor within a series of reactors. Preferred oxygen source include gaseous $O_2$ having a purity of at least 95%. Typically, an oxygen source is provided to at least one reactor in an amount ranging from about 10 to 15 kg oxygen per ton of reaction mixture.

Embodiments of methods herein include addition of a minute amounts of zirconium and/or cerium and/or nickel and/or hafnium and/or molybdenum and/or copper and/or zink containing catalytic principles to at least one reactor. The effect of such metallic additions is discussed, for example, in Partenheimer, "The effect of zirconium in metal/bromide catalysts during the autoxidation of p-xylene, Part I. Activation and changes in benzaldehyde intermediate formation," Journal of Molecular Catalysis A: Chemical, Vol. 206: p. 105-119, (2003); and Partenheimer, "The effect of zirconium in metal/bromide catalysts during the autoxidation of p-xylene, Part II. Alternative metals to zirconium and the effect of zirconium on manganese (IV) dioxide formation and precipitation with pyromellitic acid," Journal of Molecular Catalysis A: Chemical, Vol. 206: p. 131-144, (2003), the entire contents of both of which are incorporated herein by reference. Not wishing to be bound by any particular theory, it is believed that inclusion of zirconium and/or cerium into the catalyst enhances the reaction rate by providing a parallel path to the deactivation of the Co(III) exited state.

EXAMPLES

The following examples are provided to further illustrate aspects of the invention. These examples are non-limiting and should not be construed as limiting any aspect of the invention.

Example 1

Synthesis of Representative Invention Catalysts

The following exemplary procedure provides a representative method to prepare invention catalysts. In addition to the procedures described herein, numerous other procedures may be employed by one skilled in the art to prepare intermediates for and assembling the invention catalyst, including those described, for example, in Kennet J. et al. ("Applicable Zeolite Encapsulation Methods Flexible Ligand Method", J. Inclus. Phenom., Vol. 21:159-184 (1995)); Vandermade, A. W. et al. (J. Chem. Soc. Chem. Commun., Vol. 1204 (1983)); and Viswanathan et al. (J. Energy Heat and Mass Transfer, Vol. 8: 281 (1996)). The beta zeolite can be synthesized using a number of methods such as a dry gel conversion technique described, for example, in P. R. Hari Prasada Rao et al. (Chem. Commun. 1441 (1996)) and the modified aerogel protocol patent (WO 2004/050555).

The following example procedure is adapted for synthesis of the present catalyst from R. L. Wadlinger et al., U.S. Pat. No. 3,308,069, 1967. The multi-step preparation uses an in situ synthesis of beta zeolite by hydrothermal synthesis; the flexible ligand exchange method is used for incorporation of small ligands into zeolites. Step 1 involves the synthesis of an appropriate beta zeolite and calcinations to remove any organic structure directing agents to create the catalyst scaffold. In step 2 the zeolite is encapsulated in a matrix material (SiO2 in the example). Step 3 involves absorption of Co(II) and Mn(II) onto the suitably acidic zeolite. After subsequent ion exchange with the metals, the resultant metal-loaded—composite is dried. Step 4 involves coordination of the metal with nitrogen containing acids and increasing the oxidation state of the metals by oxygen addition to prepare the appropriate metal complex of the catalytic principle. This is followed by drying of the catalyst.

Step 1. Synthesis of Beta Zeolite

An amount of 39.3 g (0.654 mol) of $SiO_2$ silica gel Cab-o-sil M-5 slowly added to 171.3 g (0.407 mol) of tetraethylammonium hydroxide (TEAOH) 35 wt. % in $H_2O$, while stirring: a white gel is obtained.

A solution of 4.89 g (5.97 $10^{-2}$ mol) of $NaAlO_2$ dissolved in 69.3 ml of deionised $H_2O$ is added to the gel while stirring and manually mixing: a thicker gel is obtained.

Upon mixing and aging, the gel becomes more fluid.

The gel is stirred for 2 hours and then transferred into teflon-lined stainless-steel autoclaves. The autoclaves are closed and heated statically to 150° C. in an oven.

After 6 days at 150° C., the autoclaves are removed from the oven and allowed to cool down to room temperature.

The autoclaves contain a white-yellow gel-like precipitate and a surnatant solution. The precipitate is separated from the surnatant by centrifugation. Next, it is washed repeatedly with $H_2O$ and centrifuged until the washing has a pH<9.

The white sample is dried in an oven at 110° C. for 12 hours: 29.150 g of a white fine powder are obtained.

Powder XRD shows that the white powder is highly crystalline pure zeolite beta.

Sample characterised by: SEM, EDX and ICP-OES elemental analyses.

Si/Al=8.3, Na/Al=0.22 (EDX).

Si/Al=8.8, Na/Al=0.20 (ICP-OES).

Crystals of primary particles with a diameter of ~20-40 nm (from XRD and SEM data). Aggregates of primary particles with a diameter of ~200-300 nm.

Step 2. Inclusion of Zeolite Beta Particles into a TUD-1 Matrix

The preparation is an adaptation of the procedure outlined in P. Waller et al., Chem. Eur. J., 2004, 10, 4970.

16 g of zeolite beta (see paragraph 1) are suspended in 6.8 g (0.116 mol) of $NH_4OH$ in $H_2O$($NH_3$ ACS reagent, 28-30 wt. % $NH_3$ in $H_2O$) and in 40.65 g of deionised $H_2O$ while vigorously stirring: a white suspension is obtained.

30.45 g (0.2 mol) of triethanolamine (98%) are mixed with 25.00 g of deionised $H_2O$ and then added to the white suspension while vigorously stirring.

84.92 g (0.4 mol) of tetraethyl orthosilicate (TEOS, 98%) are added dropwise (10 g/min) while vigorously stirring. After stirring for ~1 hour, a gel is formed.

16.83 g (0.04 mol) of TEAOH 35 wt. % in $H_2O$ are added dropwise while vigorously stirring: the gel thickens until the magnetic stirring becomes ineffective.

The dense, white gel is let to age overnight. Then, it is dried in an oven for 10 hours at 99° C. Finally, it is transferred into teflon-lined stainless-steel autoclaves. The autoclaves are heated statically to 170° C. for 4 hours: a light beige solid is obtained. The solid is ground in a porcelain mortar and calcined in an oven:

30 to 600° C. at 1° C./min
600° C. for 10 hours
600 to 30° C. at 20° C./min 7.448 g of a white, fine powder are obtained.

Powder XRD shows the presence of the meso-porous structure of TUD-1 together with the main peaks of the zeolite beta included in the TUD-1 matrix.

$N_2$ physisorption measurements confirm the meso-porosity of the sample. The other data obtained from these measurements (meso-pore size: ~10 nm, $S_{BET}$ surface area: 663±14 m$^2$/g, external area: 336 m$^2$/g, total pore volume: 0.78 cm$^3$/g, micropore volume: 0.14 cm$^3$/g) are all in good agreement with the literature data.

Transmission Electron Microscopy (TEM) pictures show zeolite particles with a diameter around 26 nm homogeneously dispersed in the TUD-1 matrix.

Step 3. Absorption of Co(II) and Mn(II) onto the Acidic Zeolite 35 g of zeolite beta in a TUD-1 matrix (see paragraph 2) contain $1.69 \cdot 10^{-2}$ mol of Al. The solid is suspended in 3 L deionised H2O by stirring.

0.252 g of $Co(CH_3CO_2)_2 \cdot 4H_2O$ ($1.01 \cdot 10^{-3}$ mol, Co/Al=0.06) dissolved in 50 ml deionised H2O: the pink solution is added to the suspension while stirring.

The stirred suspension is heated to 60° C. for 12 hours (in a water bath), then at room temperature for 4 hours. The pink solid is separated by vacuum filtration and washed repeatedly with deionised $H_2O$.

The pink solid is suspended in 325 ml $CH_3CO_2H$ (glacial) by stirring.

0414 g of Mn(CH3CO2)2.4H2O ($1.69 \cdot 10^{-3}$ mol, Mn/Al=0.10) dissolved in 325 ml CH3CO2H (glacial) by stirring: the solution is added to the suspension while stirring.

The stirred suspension is heated to 60° C. for 12 hours (in a water bath), then at room temperature for 4 hours. The solid is separated by vacuum filtration and washed with 700 ml of a 1:1 solution of acetic acid and deionised $H_2O$.

The off-white wet powder is dried in an oven at 120° C. for 2 days: 34.59 g of sample are obtained.

ICP-OES analysis:
Co/Al=0.045 (efficiency of cobalt exchange: 74%).
Co weight %: 0.111%.
Mn/Al=0.079 (efficiency of manganese exchange: 79%).
Mn weight %: 0.184%.
Mn/Co=1.778 (the target was Mn/Co=2).
IR analysis does not show any change after the Co and Mn exchange.

Step 4. Coordination of Metal-Exchanged Zeolites with Nitrogen Acids

A sample containing 0.5 g of a Co and Mn exchanged zeolite beta s (see step 3) containing $2.04 \cdot 10^{-4}$ mol of Co+Mn was used.

$6.0 \cdot 10^{-3}$ mol of NaOH (0.24 g) were dissolved in 4 g of deionised $H_2O$. $5.0 \cdot 10^{-3}$ mol of nicotinic acid (0.62 g) were added to the aqueous solution and dissolved by stirring. Next, $4.08 \cdot 10^{-3}$ mol (i.e. 2 moles per mole of metal, as in the complexes) of acetic acid (0.025 g) were added while stirring. A colourless transparent solution with pH≈11 was obtained.

The aqueous solution was added to the 0.5 g of zeolite sample while stirring: a light brown suspension was obtained.

$2.0 \cdot 10^{-3}$ mol of $H_2O_2$ were added as 0.060 g of a solution obtained by mixing 0.150 g of $H_2O_2$ 35 wt. % aqueous solution with 0.314 g of deionised $H_2O$: bubbles evolved and the brown colour of the suspension becomes darker.

After stirring for 1 hour, $2.5 \cdot 10^{-4}$ mol of NaBr (0.026 g) previously dissolved in 0.5 g of deionised H2O were added to the suspension while stirring.

After stirring for 30 minutes, the suspension was filtered under vacuum on a Buchner filter and washed with 100 ml of a 1:1 (in volume) solution of ethanol and acetic acid.

The solid residue was dried overnight in an oven at 110° C.: 0.44 g of a light grey powder were obtained.

Example 2

Exemplary Procedure for Preparation of Representative Aromatic Carboxylic Acid

A preferred embodiment for the production of terephthalic acid is illustrated in FIG. 1.

Invention methods provided the following advantageous properties due, in part, to the low conversion of para-xylene in the oxidation reactor.

The temperature increase of the reaction mixture is sufficient to dissipate the heat of reaction and thus, there is no need to cool the oxidation reactor.

The oxygen applied to the oxidation reactor is dissolved and does not form a separate vapor phase.

The water produced by the chemical reaction will not form a separate liquid phase.

The terephthalic acid produced by the chemical reaction will not form a separate solid phase.

Reactors

Oxidation of p-xylene is performed in continuous oxidation reactors, conceived in such a way to avoid back-mixing, wherein each reactor is fed with an oxygen source. Reactors containing fluidized beds with intrinsic recycle of catalyst, fixed beds with static arrangement of catalyst, or cross flow beds and membrane reactors may also be used. As exemplified in FIG. 1, the oxidation reactor may be composed of one or several reaction vessels.

Oxidation Reaction

As shown in FIG. 1, an oxygen source and p-xylene is fed into the oxidation reactor. Terephthalic acid (TPA), produced in the oxidation reaction, remains soluble in p-xylene throughout the course of the oxidation reaction. Thus, the oxidation reaction mixture is essentially a single-phase liquid mixture. Operating conditions in the oxidation reactor are such that no second phase will be formed, neither as a vapor, liquid, or solid.

Invention catalysts, which remain solid suspended in p-xylene, may be added to the oxidation reactor in the form of a slurry that leaves the reactor with the reaction mixture or can be arranged in various forms such as fixed bed, radial bed, membranes and the like.

The reaction mixture is de-pressurized over a throttle valve after leaving the oxidation reactor.

Separation of Invention Catalyst

The solid invention catalyst used in the oxidation reaction, when used in a slurry or fluidized bed configuration, is separated (e.g., by a hydrocyclone) prior to separation of the reaction products from the reaction mixture. After separation, invention catalysts are rinsed with fresh p-xylene, recycled dry p-xylene or a combination of such streams in a counter-current wash. Invention catalyst may then be recycled as a slurry back into the oxidation reactor for continuous oxidation reactions, along with the balance make-up of p-xylene and the bulk of the recycled solvent.

In embodiments where the catalyst contacts the reaction mixture in the form of a fixed or fluidized bed, the catalyst will not leave the oxidation reactor. As such, separation of the catalyst from the reaction mixture is not necessary.

Pressurization Decreases

During de-pressurization, the reaction mixture will start to boil and as a result the temperature of both the vapor phase and the liquid phase will start to decrease. As a result of the boiling, water, gaseous components, and p-xylene from the oxidation reactor will vaporize, leaving behind the produced terephthalic acid in a solid form.

Removal of Reaction Impurities

As shown in FIG. 1, water created by the oxidation reaction is removed from the remaining solvent stream (containing p-xylene, water and residual impurities) by distillation or sequential flashing, during which the volatile side products are also removed. Non-volatiles may be removed as a purge side stream from the bottom of the separation stage, to be processed separately to remove heavy components and prevent build-up in the reactor.

Crystallization of Terephthalic Acid

The catalyst-free main stream is cooled after catalyst separation, leading to crystallization of terephthalic acid. Crystals are recovered (e.g., by a hydrocyclone or filtration) from the solvent and processed for subsequent use by countercurrent washing with fresh p-xylene.

Continuous Recycling into Oxidation Reactors

The "dry" p-xylene, together with several other p-xylene recuperation streams (e.g. decantation from a flash or distillation top fraction, the catalyst washing, etc.) are fed back into the recycle solvent stream to the oxidation reactor. This recycled solvent may be split in several washing streams (such as for rinsing the recovered terephthalic acid crystals, the recovered catalyst, etc.) but these streams of p-xylene are eventually collected and fed to the oxidation reactor directly or to prepare the slurry for the recycled catalyst. To the combined recycle the make-up for the catalyst and the bromine containing component is also added.

The invention claimed is:

1. A catalyst system comprising a catalytically active principle incorporated in zeolite crystallites attached to a support or incorporated into a matrix, the crystallites having a diameter of between 20 and 300 nm and said catalytically active principle having a formula corresponding to:

$CoMn_2(O)(R-COO)_6L^1_{k1}L^2_{k2}$ wherein:

R is an optionally substituted $C_1$-$C_4$ alkyl;

$L^1$ is an optionally substituted nitrogen containing carboxylic acid or carboxylate;

$L^2$ is selected from the group consisting of $H_2O$, an optionally substituted $C_1$-$C_4$ alkyl containing carboxylic acid, an optionally substituted $C_5$-$C_6$ cycloalkyl or heterocycle, an optionally substituted $C_5$-$C_6$ heteroaryl or aryl; and k1 is 1, 2, or 3;

k1+k2=3;

wherein the zeolite has an Si/Al atomic ratio of at least 8.

2. The catalyst system of claim 1, wherein R of said catalytically active principle is —$CH_3$ or —$C_2H_5$.

3. The catalyst system of claim 1, wherein $L^1$ of said catalytically active principle is selected from the group consisting of picolinic acid, nicotinic acid, and i-nicotinic acid, or salt thereof and independently of the selection of $L^1$, $L^2$ is $CH_3COOH$ or $H_2O$.

4. A catalyst system comprising a catalytically active principle incorporated in zeolite crystallites attached to a support or incorporated into a matrix, the crystallites having a diameter of between 20 and 300-nm and said catalytically active principle having a formula corresponding to:

$CoMn_2(O)(R-COO)_{6-k3}L^3_{k3}L^4_{k4}$ wherein:

R is an optionally substituted $C_1$-$C_4$ alkyl;

$L^3$ is an optionally substituted nitrogen containing carboxylate;

$L^4$ is selected from the group consisting of $H_2O$, an optionally substituted nitrogen containing carboxylic acid, an optionally substituted $C_1$-$C_4$ alkyl containing carboxylic acid, an optionally substituted $C_5$-$C_6$ cycloalkyl or heterocycle, and an optionally substituted $C_5$-$C_6$ heteroaryl or aryl;

k3 is 1, 2, or 3;

k3+k4=3.

5. The catalyst system of claim 1, wherein said zeolite belongs to a class selected from the group consisting of MEI, beta (*BEA), members of the associated disorder families, and mixtures thereof.

6. The catalyst system of claim 1, wherein said crystallites of zeolite are embedded, grafted or encapsulated in a mesoporous matrix comprising $SiO_2$ and/or carbon.

7. A process of preparing a catalyst system according to claim 1, wherein crystallites of a zeolite having an crystallite size of between 20 and 300 nm, and having an Si/Al atomic ratio of at least 8 are provided with a catalytically active principle, the process comprising synthesizing said catalytically active principle within the crossings of channels within the zeolite.

8. The catalyst system of claim 2, wherein $L^1$ of said catalytically active principle is selected from the group consisting of picolinic acid, nicotinic acid, and i-nicotinic acid, or salt thereof and independently of the selection of $L^1$, $L^2$ is $CH_3COOH$ or $H_2O$.

9. The catalyst system of claim 8, wherein:

said zeolite belongs to a class selected from the group consisting of MEI, beta (*BEA), members of the associated disorder families, and mixtures thereof; and crystallites of zeolite are embedded, grafted or encapsulated in a mesoporous matrix comprising $SiO_2$ and/or carbon.

10. The catalyst system of claim 4, wherein:

said zeolite belongs to the class MEI or beta (*BEA) or is a member of the associated disorder families, or is a mixture thereof;

crystallites of zeolite are embedded, grafted or encapsulated in a meso-porous matrix including $SiO_2$ and/or carbon.

11. A process of preparing the catalyst system according to claim 2, wherein crystallites of a zeolite having a crystallite size of between 20 and 300 nm and having an Si/Al atomic ratio of at least 8 are provided with a catalytically active principle, the process comprising synthesizing said catalytically active principle within the crossings of channels within the zeolite.

12. A process of preparing the catalyst system according to claim 4, wherein crystallites of a zeolite having a crystallite size of between 20 and 300 nm and having an Si/Al atomic ratio of at least 8 are provided with a catalytically active principle, the process comprising synthesizing said catalytically active principle within the crossings of channels within the zeolite.

* * * * *

UNITED STATES PATENT AND TRADEMARK OFFICE
CERTIFICATE OF CORRECTION

PATENT NO. : 8,187,992 B2
APPLICATION NO. : 11/793468
DATED : May 29, 2012
INVENTOR(S) : De Meyer et al.

Page 1 of 1

It is certified that error appears in the above-identified patent and that said Letters Patent is hereby corrected as shown below:

In the Specifications

Column 11, line 21, "$83^4$" should read --834--.

Signed and Sealed this
Twenty-third Day of April, 2013

Teresa Stanek Rea
*Acting Director of the United States Patent and Trademark Office*